United States Patent
Ninomiya et al.

(10) Patent No.: US 6,703,013 B1
(45) Date of Patent: Mar. 9, 2004

(54) POLYSTYRENE SULFONATE-CONTAINING GEL PREPARATION

(75) Inventors: Hideaki Ninomiya, Nagoya (JP); Masahiro Nakajima, Nagoya (JP); Toshiyuki Kouzaki, Nagoya (JP); Masaki Ando, Nagoya (JP); Fumio Higuchi, Nagoya (JP)

(73) Assignee: Sanwa Kagaku Kenkyusho Co., Ltd., Aichi (JP)

( * ) Notice: Subject to any disclaimer, the term of this patent is extended or adjusted under 35 U.S.C. 154(b) by 0 days.

(21) Appl. No.: 09/508,539

(22) PCT Filed: Oct. 15, 1998

(86) PCT No.: PCT/JP98/04656

§ 371 (c)(1),
(2), (4) Date: Apr. 5, 2000

(87) PCT Pub. No.: WO99/20247

PCT Pub. Date: Apr. 29, 1999

(30) Foreign Application Priority Data

Oct. 16, 1997 (WO) .............................. PCT/JP97/03740

(51) Int. Cl.[7] .................. A61K 37/74; A01N 25/00
(52) U.S. Cl. ............................... 424/78.1; 514/944
(58) Field of Search ............... 424/78.1; 166/282; 514/944

(56) References Cited

U.S. PATENT DOCUMENTS 3,480,084 A * 11/1969 Eilers
4,375,461 A * 3/1983 Gander et al. ............. 424/56
4,837,015 A * 6/1989 Olsen
5,093,130 A * 3/1992 Fujii et al. ................ 424/463

FOREIGN PATENT DOCUMENTS

JP       59116484       * 7/1984

* cited by examiner

*Primary Examiner*—Thurman K. Page
*Assistant Examiner*—Blessing Fubara
(74) *Attorney, Agent, or Firm*—Rader, Fishman & Grauer PLLC

(57) ABSTRACT

The invention relates to a polystyrene sulfonate-containing gel preparation for therapy of hyperpotassemia, wherein the particle size of polystyrene sulfonate is controlled within the range of at least 5–100 μm, the viscosity of its solution before gelation is adjusted depending on the particle size by adding a thickening agent, and the polystyrene sulfonate particles after gelation is uniformly dispersed therein. More preferably, a water-displacing agent is contained, whereby the amount of water in the preparation is reduced. This gel preparation does not cause a sense of foreign matter or a sense of roughness in the oral cavity upon ingestion and intake, thus making it unnecessary to drink water for ingestion, and further its water content is low, so that control of water intake is made easy, even in the case of a patient with renal insufficiency who is subjecting to restriction in intake of water to significant improve the quality of life of the patient.

5 Claims, 1 Drawing Sheet

♦—♦ : 25 μm
■—■ : 50 μm
▲—▲ : 75 μm
●—● : 100 μm

POLYSTYRENE SULFONATE-CONTAINING GEL PREPARATION

TECHNICAL FIELD

The present invention relates to a polystyrene sulfonate-containing preparation which can be easily taken with a drastically reduced intake of water for ingestion, and particularly to a gel therapeutic agent for hyperpotassemia, which comprises polystyrene sulfonate as an active ingredient.

BACKGROUND ART

Conventional therapies applied to patients with hyperpotassemia include calcium gluconate therapy, glucose-insulin therapy, sodium bicarbonate therapy, saline therapy or a combination thereof for relative emergency cases, or dialysis therapy and cation-exchange therapy based on administration of cation-exchange resin such as polystyrene sulfonate for non-emergency cases. Among these therapies, the cation-exchange therapy involving removing potassium from the body by replacement of potassium ions in intestinal tracts is generally conducted for patients with chronic renal insufficiency, and in this therapy, a daily dosage of 15 to 30 g polystyrene sulfonate for an adult person is divided into 2 to 3 portions and each portion is suspended in 30 to 50 ml water and orally administered. However, polystyrene sulfonate is a powder which is hardly dissolved in water and it should be taken in a large amount, so it feels strongly unpleasant in the oral cavity upon ingestion, and it is noted that there are many cases where compliance with clinician's instructions is not obeyed.

The polystyrene sulfonate when suspended in water is easily precipitated at the bottom of a cup, thus making it difficult to take the whole dose all at once, so some patients take powdery sulfonate polystyrene with water in the oral cavity without previously suspending it. In this case, there is a possibility that the polystyrene sulfonate is not uniformly dispersed in digestive tracts and forms agglomerates, thus failing to bring about the desired pharmaceutical effect. Further, the polystyrene sulfonate when taken in the form of powder feels strongly unpleasant in the oral cavity, to become a great mental burden on the patient. Hence, the polystyrene sulfonate gives a remarkably unpleasant feeling in the oral cavity, and according to the present application method, it is difficult to take the whole of a prescribed dose all at once, so under the present circumstances, the patient drinks a large amount of water to take it, which is contraindicated for renal insufficiency.

Recently, the method of administering the pharmaceutical preparation is recently devised in some hospitals, and it is reported that the improvement of compliance is attempted by manufacturing calcium polystyrene sulfonate etc. into jelly preparations {"Shinryo To Shinyaku", Vol. 29, No. 2, p. 514 (1992), "Shinryo To Shinyaku", Vol. 31, No. 11, p. 1911 (1994); and "Iyaku No Mon", Vol. 31, No. 3, p. 190 (1991)}.

However, even in the above-described polystyrene sulfonate-containing jelly preparations, there remain the following problems:

(a) The polystyrene sulfonate-containing jelly preparations reported in the above literatures feel rough like sand, and are inferior in a sense of ingestion. This sense of roughness remains considerably in the oral cavity, and especially 50% or more polystyrene sulfonate is precipitated at the bottom of a vessel at the time of manufacturing the jelly preparation, and thus a sense of significant roughness is felt upon ingestion of the jelly preparation sedimented at the bottom of the vessel, and the removal of this unpleasant sense or sense of foreign matter requires drinking water, which results in an excessive intake of water to cause a great problem for patients with renal insufficiency.

(b) While the variability of contents in jelly confectionery as general food is acceptable at certain degrees, the amounts of contents in the jelly preparation as a pharmaceutical preparation should be strictly guaranteed. However, the majority of polystyrene sulfonate is precipitated upon introduction into a solution before gelation, so it is difficult to set a predetermined content of said salt in the jelly preparation, and accordingly it is almost impossible to produce a large amount of a jelly preparation with a constant content of said salt. To prepare a large amount of a jelly preparation with a constant content of polystyrene sulfonate, it is conceivable that a predetermined amount of said salt is introduced into each vessel and then a solution for gelation is poured into it. However, the polystyrene sulfonate in the vessel is poor in uniform dispersibility, and thus upon ingestion of a part containing a large content of said salt, those who take it feel significantly unpleasant in the oral cavity. Therefore, manual manufacturing of the jelly preparation, such as dispensing it little by little rapidly with stirring, is necessary under the present circumstances, but this makes the operation complicated and productivity lowered. After all, it is very difficult or impossible to prevent the polystyrene sulfonate from being unevenly distributed in the jelly preparation.

(c) The amount of water in the conventional polystyrene sulfonate-containing jelly preparation is at least 100 ml/preparation, and accordingly if it is administered 3 times every day, the intake of water will be at least 300 ml/day. Further, if water is taken in an amount of 50 ml for each administration to relieve the significant unpleasant feeling, the amount of water taken for the administration is further increased to be more than 450 ml/day. However, the daily intake of water for a patient with renal insufficiency is limited to 400–700 ml in order to relieve the burden on the kidney. Accordingly, if the polystyrene sulfonate-containing jelly preparation is administered, the amount of water (including drinking water) which can be taken from other materials than said preparation is made less than half of the usual amount or is very small in some cases, thus significantly impairing the life or quality of life (QOL) of the patient and bringing about a mental burden on the patient.

DISCLOSURE OF INVENTION

An object of the present invention is to solve the above-described prior art problems all at once. That is, the problem to be solved by the invention is to provide polystyrene sulfonate-containing gel preparations with a reduced content of water and with a reduced unpleasant feeling at the time of administration or ingestion, whereby the amount of water taken for administration, as a great problem in patients with renal insufficiency, can be reduced. A further object is to guarantee the content of polystyrene sulfonate in a pharmaceutical preparation and to enable production thereof in a large amount at the industrial level.

The polystyrene sulfonate-containing gel preparation according to the present invention is characterized in that the particle diameter of polyethylene sulfonate is made uniform within the range of at least 5–100 μm. Further, it is characterized in that the viscosity before gelation is adjusted depending on its particle size by adding a thickening agent and the polystyrene sulfonate particles after gelation are uniformly dispersed. More preferably, it is characterized in that a part of contained water is replaced by containing a water-displacing agent.

Hereinafter, the gel preparation of the present invention is described in more detail.

At the time of preparing the polystyrene sulfonate-containing gel preparation of the present invention, adjustment of the viscosity of its solution before gelation is conducted so that a prescribed amount of the active ingredient is contained in an uniformly dispersed state in the preparation without deteriorating the ability of said salt on ion exchange, and simultaneously the unpleasant sense of roughness in the oral cavity upon administration is reduced. As a result of reduction of the unpleasant sense of roughness in the oral cavity, the patient can reduce water intake for ingestion of said preparation.

The viscosity of the solution at 50° C. before gelation is adjusted by the thickening agent specifically to 50 cP or more in case where the particle diameter of polystyrene sulfonate is 5–25 μm, to 100 cP or more in case of 5–50 μm, to 300 cP or more in case of 5–75 μm, and to 1000 cP or more in case of 5–100 μm. The present inventors have found that if dispensed into each vessel after this adjustment of viscosity, a gel preparation containing a prescribed amount of the salt in a uniformly dispersed state can be obtained without precipitating polystyrene sulfonate particles (see Test Example 1 below) and further that the unpleasant sense of roughness in the oral cavity upon ingestion of said preparation is reduced.

Strictly speaking, if polystyrene sulfonate with a particle size of 5 to X μm is used to prepare the gel preparation, the viscosity of its solution is adjusted to that viscosity read from FIG. 2 in the appended drawings at which particles having a particle diameter of X μm are not precipitated, whereby the desired preparation can be obtained.

The above-mentioned viscosity of 50 cP is not a lower limit, and the viscosity has a further lower value if the majority of particles have a diameter of e.g. 5–10 μm, and for example, the viscosity before gelation can be adjusted to 50 cP or so by incorporating a small amount of large particles (e.g. 100 μm) into particles having a diameter of 20–35 μm.

This adjustment of viscosity can be conducted by using at least one substance of various thickening agents, sugars and sugar alcohols. In this case, the thickening agent is not particularly limited, and mention can be made of natural polysaccharides such as xanthan gum and guar gum, water-soluble derivatives of cellulose, such as hydroxypropyl cellulose and carboxymethyl cellulose, starch derivatives such as carboxymethyl starch, alginic acid derivatives such as alginic acid polypropylene glycol ester, and polyacrylic acid derivatives. Further the sugars and sugar alcohols are not particularly limited, and mention can be made of various sugars such as glucose, xylose, maltose, sucrose, lactose, dextrin, invert sugars, and starch hydrolysate, and sugar alcohols such as sorbitol, mannitol, xylitol, maltitol and hydrogenated malt starch hydrolysate. In the present specification, all the thickening agents, sugars and sugar alcohols are collectively referred to as thickening agent, as a matter of convenience.

The gel preparation of the present invention is defined based on the adjustment of the viscosity of the solution before solidification but not of the final preparation, as described above, and this is because it is very difficult or impossible to define it in the state of the final preparation, and the gel preparation is defined specifically in terms of the viscosity of its solution at a temperature of 50° C.; this is because this temperature is a general dispensing temperature when a gel preparation is prepared.

The reason for controlling the particle diameter of polystyrene sulfonate in the present invention within the range of at least 5–100 μm is for further reducing the unpleasant sense of roughness in the oral cavity upon ingestion. That is, the present inventors have noticed that the sense of ingestion is not sufficiently improved by merely attempt to uniformly disperse polystyrene sulfonate with the above thickening agent, and after repeated trial and error, the present inventors have found that the sense of roughness in the oral cavity is significantly relieved by controlling the particle diameter of said salt, that is, by making the particles small. Then, the present inventors concluded that if the particle diameter is made 100 μm or less, the gel or jelly preparation can be administered as such without drinking water (see Test Example 2 below). Accordingly, the diameter is preferably smaller within this range. The diameter is preferably 5 to 75 μm, more preferably 5 to 50 μm, and most preferably 5 to 25 μm.

The polystyrene sulfonate used in the present invention is not particularly limited insofar as it is a pharmaceutically acceptable salt, and its calcium salt and sodium salt can be mentioned. In the commercial polystyrene sulfonate powder for pharmaceutical preparations, the content of 5 μm or less fine particles is regulated to 0.1% or less in order to prevent the particles from being precipitated on tissues in a reticuloendothelial system after absorption via mucosa, but particles of a relatively large size of 100 to 200 μm account for 20% or more of the whole. The particles of a desired size can be easily obtained from the commercial polystyrene sulfonate powder for pharmaceutical preparations by a general method, that is, by sieving or with a grinding classifying machine.

A water-displacing agent is not necessarily required to be contained in the gel preparation of the present invention, but nevertheless it is preferably contained. This is to substitute for a part of water in the gel preparation, whereby the water content in the gel preparation can be minimized without reducing the gel volume. The intake of water, accompanying ingestion of said preparation, can be minimized without deterioration of a sense of ingestion.

The water-displacing agent is not particularly limited, and it is possible to use at least one substance of glycerin, propylene glycol, polyethylene glycols, sugars and sugar alcohols. The sugars include glucose, xylose, maltose, sucrose, lactose, dextrin, invert sugars and starch hydrolysates, and sugar alcohols include sorbitol, mannitol, xylitol, maltitol, and hydrogenated malt starch hydrolysate. These may overlap with the above thickening agent.

The water-displacing agent is not essential because in the present invention, the amount of water can be simply reduced in order to decrease the water content in the gel preparation. If the amount of water used is reduced in the conventional polystyrene sulfonate-containing gel preparation, the gel (jelly) volume is also reduced as shown in Test Example 6, and simultaneously a sense of ingestion is significantly worsened thus making it inevitable to drink further water after all, so the amount of water used could not be simply reduced. That is, reduction of the amount of water used (reduction of the gel volume) was incompatible with improvement of the sense of ingestion. However, it was revealed that in the polystyrene sulfonate-containing gel preparation of the present invention, even if the amount of water used is reduced in order to decrease the gel volume, the sense of ingestion is worsened only slightly as a result of significant improvement of the sense of ingestion by uniform dispersion with the above thickening agent and by regulating the particle diameter to 5–100 μm (see Test Examples 4 and 6 below). This means that the present invention achieves reduction of the amount of water used (reduction of the gel volume) and simultaneous improvement of the sense of ingestion, so that even if there is no water-displacing agent, sufficient reduction of the water content and improvement of the sense of ingestion can be achieved, as compared with the conventional products.

The amount of water contained in the gel preparation disclosed as the present invention is 60 ml or less every 5 g polystyrene sulfonate or 12 ml per every 1 g thereof, and water is contained preferably in a less amount in the range where the uniform dispersion of polystyrene sulfonate and improvement of the sense of ingestion are achieved. For easy handling of the product, it is considered most preferable that a single dose of 5 g polystyrene sulfonate has a gel volume of about 20 to 30 ml, and the amount of water contained in this case is smaller than said gel volume, that is, about 12 to 20 ml is considered most preferable. If the amount of water is further reduced, it is possible that the ingredients contained are hardly dissolved or the polystyrene sulfonate cannot be uniformly dispersed.

The gelling agent for preparing the gel preparation of the present invention is not particularly limited, and mention can be made of agar, carrageenan, locust bean gum, alginic acid and salts thereof, gelatin, pectin, carboxymethylcellulose, and starch.

The gel preparation of the present invention can be prepared in accordance with a conventional method of preparing jelly confectionery, that is, by dissolving various components by heating, dispensing the solution into a suitable vessel, and cooling it. The appearance is in the form of solid such as jelly, pudding, Bavarian cream and gummi to the form of starch paste, and it can be dispensed in a cup, bag, tube etc. and packaged. Further, additives such as pH adjuster, flavor, coloring matter, sweetener and antimicrobial agent can be contained, if necessary.

Hereinbefore, the gel preparation of the present invention has been described. By combination of the means described above, the water content in the polystyrene sulfonate-containing gel preparation of the present invention was significantly reduced. The water content in the gel preparation of the present invention described in the Production Examples is 15 to 60 ml per every 5 g polystyrene sulfonate, and the water content can be reduced to 15 to 60% of the conventional gel preparations containing said salt (100 ml per every 5 g polystyrene sulfonate). Further, there is little need for drinking water for ingestion of said preparation, and as shown in Test Example 3, the total intake of water is ¼ to ⅕ as compared with that of the conventional preparation, and 300 to 400 ml of water intake daily could be reduced. A daily amount of water intake is limited to 400 to 700 ml for patients with renal insufficiency, but 400 ml or more water is taken in total when the conventional polystyrene sulfonate preparation is ingested, thus leading to consumption of ½ or more of the limited amount of water or even the total amount in some cases. As a result, there arises a need for significant reduction of the amount of water taken from other materials (food and drinking water) than said preparation, resulting in significant deterioration of "quality of life" of the patient. In consideration of these, it is understood that the effect of reducing the water intake by 300–400 ml/day according to the invented preparation is extremely significant. As a result, it is possible to control patient's water intake strictly and to further improve "quality of life" of the patient significantly.

The preparation of the present invention having an average water content is used in Test Example 3, but if the preparation of the present invention having a less water content is used as shown in Production Example 10 or 13, the daily amount of water taken when said preparation is ingested is reduced to about 50 ml, to make its effect more significant.

In the polystyrene sulfonate-containing gel preparation as a pharmaceutical preparation, the content of said salt as the active ingredient should be strictly guaranteed. In the conventional preparation, the content of the polystyrene sulfonate as the active ingredient or its effective amount for administration have not been guaranteed as described above. In the polystyrene sulfonate-containing gel preparation of the present invention, the polystyrene sulfonate as the active ingredient is strictly guaranteed as an effective amount, as described above, and a polystyrene sulfonate preparation conforming to standards as a pharmaceutical preparation can be produced for the first time at the industrial level.

BEST MODE FOR CARRYING OUT THE INVENTION

Hereinafter, the present invention shall be explained in more detail and in concrete with reference to Test Examples, Production Examples, and Control Production Examples.

Test Example 1 (Particle size of polystyrene sulfonate and dispersibility in gel preparation)

| | |
|---|---|
| Calcium polystyrene sulfonate | 5 g |
| Mean particle diameter: 24.1 μm | |
| (particle size distribution: 20–35 μm), | |
| Mean particle diameter: 46.0 μm | |
| (particle size distribution: 40–60 μm), | |
| Mean particle diameter: 73.4 μm | |
| (particle size distribution: 70–80 μm) or | |
| Mean particle diameter: 103 μm | |
| (particle size distribution: 90–120 μm). | |
| Agar | 1 g |
| Purified water | 42 ml |
| Red wine | 20 ml |
| D-sorbitol | 38 g |
| Carboxymethylcellulose-Na(CMC-Na) | suitable amount |

After agar as a gelling agent was heated and dissolved in purified water, red wine was added thereto, and further D-sorbitol containing sodium carboxymethyl cellulose (CMC-Na) as a thickening agent dispersed therein was added and mixed therewith. Then, the resulting solution was filtered and cooled to 50° C., calcium polystyrene sulfonate was added and uniformly mixed therewith, and the mixture was dispensed into a vessel and cooled in a refrigerator to cause gelation thereof.

The prepared gel preparation sample was taken out from the vessel and cut into 5 equal round slices as test samples (the uppermost sample I—the lowermost sample V, the thickness of each test sample: about 1 cm). Each of the test samples was separately heated and dissolved. The resulting sol was filtered through a glass filter (G4), and the residue (polystyrene sulfonate) on the filter was washed with 100 ml hot water and then dried at 80° C. for 5 hours under reduced pressure, and the weight of the polystyrene sulfonate was measured.

The viscosity of the solution for preparing the gel preparation sample was adjusted by varying the amount of sodium carboxymethyl cellulose added.

Figure 1:
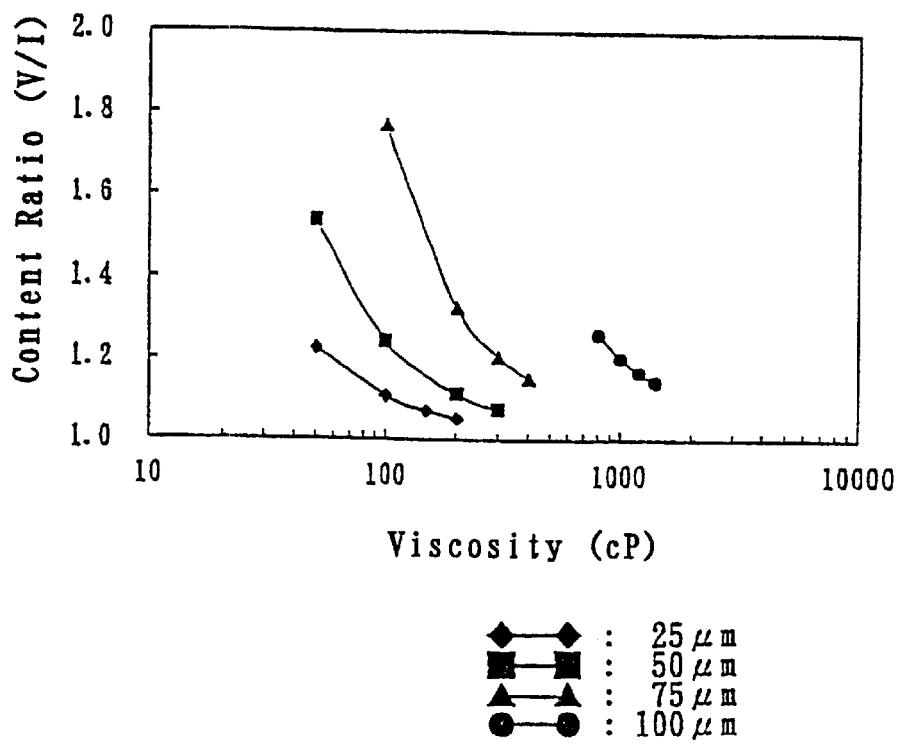
FIG. 1 is a graph showing the result where gel preparations were prepared by using polystyrene sulfonate different in the particle diameter distribution, and the relationship between the viscosity of its solution before gelation and the distribution in the vertical direction of polystyrene sulfonate particles in the gel preparation was examined for each diameter of said salt particles.
Figure 2:
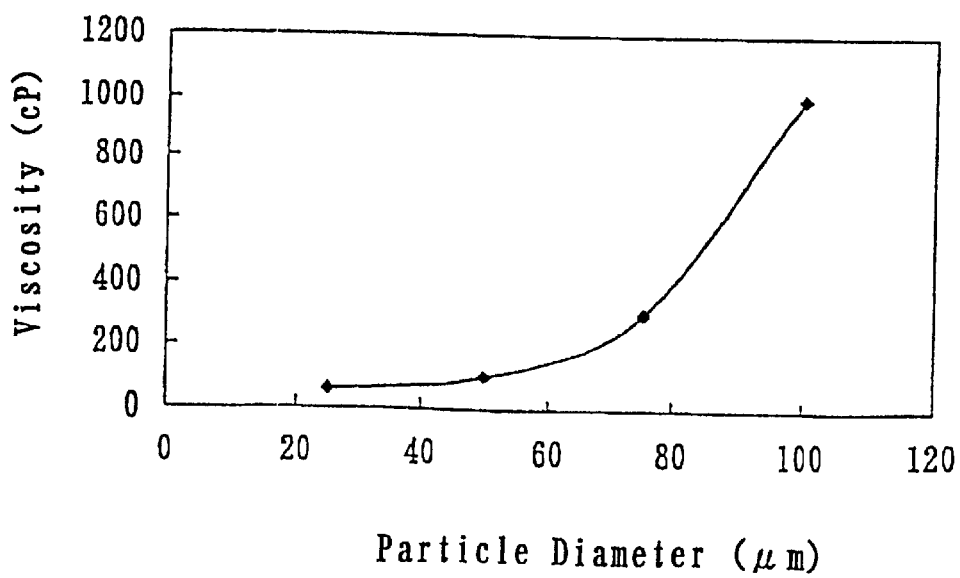
FIG. 2 is a graph showing the relationship between the particle diameter and the viscosity of its solution before gelation, at which the polystyrene sulfonate with each particle diameter can be uniformly dispersed in the gel preparation.

Results are shown in FIG. 1. As is evident from the figure, the ratio (V/I) of the polystyrene sulfonate content in the vertical direction is reduced to approach 1 by increasing the viscosity depending on the particle diameter, so that the polystyrene sulfonate can be dispersed uniformly in the preparation. The viscosity of the solution just before dispensation at 50° C., at which viscosity the polystyrene sulfonate with each particle diameter can be uniformly dispersed in the gel preparation, that is, the viscosity at which the polystyrene sulfonate content in the respective parts (I to V) of the preparation is in the range of 90 to 110% [or the viscosity at which the polystyrene sulfonate content in each sample is in the range of 0.9 to 1.1 g (assuming that there is a tolerance of 10%) because in the present test, 5 g polystyrene sulfonate were used to prepare a cylindrical gel preparation and divided into 5 equal portions to obtain samples I to V, so each sample must contain 1 g if it is uniformly dispersed; in other words, the viscosity at which V/I is 1.22 or less] was determined to be in an upper part in a curve shown in FIG. 2.

Production Example 1

| Calcium polystyrene sulfonate (particle size distribution: 5–100 µm) | 5 g |
|---|---|
| Agar | 0.5 g |
| Carboxymethyl cellulose-Na(CMC-Na) | 0.9 g |
| Purified water | 43.6 ml |
| Aspartame | 0.025 g |

The above respective ingredients were used to prepare the calcium polystyrene sulfonate-containing gel preparation. That is, agar as a gelling agent was heated and dissolved in purified water, then sodium carboxymethyl cellulose (CMC-Na) as a thickening agent and aspartame as a sweetener were added, and these were mixed and dissolved. The resulting solution was filtered and cooled to 50° C., calcium polystyrene sulfonate was added and mixed uniformly therewith, and the mixture was dispensed into a vessel and cooled in a refrigerator to obtain the desired gel preparation. The viscosity of the solution at 50° C. was adjusted to 3500 cP (this viscosity measurement was conducted after the addition of calcium polystyrene sulfonate; this also applies to the following Production Examples).

Production Example 2

| Calcium polystyrene sulfonate (particle size distribution: 5–50 µm) | 5 g |
|---|---|
| Agar | 0.5 g |
| Carboxymethyl cellulose-Na(CMC-Na) | 0.9 g |
| Purified water | 43.6 ml |
| Aspartame | 0.025 g |

The desired gel preparation was obtained by using the above respective ingredients in the same manner as in Production Example 1. The viscosity of the solution at 50° C. was adjusted to 3300 cP.

Production Example 3

| Calcium polystyrene sulfonate (particle size distribution: 5–100 µm) | 5 g |
|---|---|
| Agar | 0.5 g |
| Carboxymethyl cellulose-Na(CMC-Na) | 0.9 g |
| Purified water | 33.6 ml |
| Powdered malt starch hydrolysate | 10.0 g |

The desired gel preparation was obtained by using the above respective ingredients in the same manner as in Production Example 1 (The powdered malt starch hydrolysate was added together with sodium carboxymethyl cellulose). The viscosity of the solution at 50° C. was adjusted to 3900 cP.

Production Example 4

| Calcium polystyrene sulfonate (particle size distribution: 5–50 µm) | 5 g |
|---|---|
| Agar | 0.5 g |
| Carboxymethyl cellulose-Na(CMC-Na) | 0.9 g |
| Purified water | 33.6 ml |
| Powdered malt starch hydrolysate | 10.0 g |

The desired gel preparation was obtained by using the above respective ingredients in the same manner as in Production Example 3. The viscosity of the solution at 50° C. was adjusted to 3850 cP.

Production Example 5

| Calcium polystyrene sulfonate (particle size distribution: 5–100 µm) | 5 g |
|---|---|
| Agar | 1 g |
| Purified water | 42 ml |
| Red wine | 20 ml |
| D-sorbitol | 38 g |
| Carboxymethyl cellulose-Na(CMC-Na) | 0.29 g |

The above respective ingredients were used to prepare the calcium polystyrene sulfonate-containing gel preparation. That is, agar as a gelling agent was heated and dissolved in purified water, then red wine was added, and D-sorbitol containing sodium carboxymethyl cellulose (CMC-Na) as a thickening agent dispersed therein was added and mixed therewith. Then, the resulting solution was filtered and cooled to 50° C., calcium polystyrene sulfonate was added and mixed uniformly therewith, and the mixture was dispensed into a vessel and cooled in a refrigerator to obtain the desired gel preparation. The viscosity of the solution at 50° C. was adjusted to 1013 cP.

Production Example 6

| Calcium polystyrene sulfonate (particle size distribution: 5–75 μm) | 5 g |
|---|---|
| Agar | 1 g |
| Purified water | 42 ml |
| Red wine | 20 ml |
| D-sorbitol | 38 g |
| Carboxymethyl cellulose-Na(CMC-Na) | 0.15 g |

The desired gel preparation was obtained by using the above respective ingredients in the same manner as in Production Example 5. The viscosity of the solution at 50° C. was adjusted to 302 cP.

Production Example 7

| Calcium polystyrene sulfonate (particle size distribution: 5–50 μm) | 5 g |
|---|---|
| Agar | 1 g |
| Purified water | 42 ml |
| Red wine | 20 ml |
| D-sorbitol | 38 g |
| Carboxymethyl cellulose-Na(CMC-Na) | 0.04 g |

The desired gel preparation was obtained by using the above respective ingredients in the same manner as in Production Example 5. The viscosity of the solution at 50° C. was adjusted to 111 cP.

Production Example 8

| Calcium polystyrene sulfonate (particle size distribution: 5–25 μm) | 5 g |
|---|---|
| Agar | 1 g |
| Purified water | 42 ml |
| Red wine | 20 ml |
| D-sorbitol | 38 g |

The desired gel preparation was obtained by using the above respective ingredients in the same manner as in Production Example 5. The viscosity of the solution at 50° C. was adjusted to 54 cP.

Production Example 9 (Gel volume was set at ½ of that in Production Example 7)

| Calcium polystyrene sulfonate (particle size distribution: 5–50 μm) | 5 g |
|---|---|
| Agar | 0.5 g |
| Purified water | 21 ml |
| Red wine | 10 ml |
| D-sorbitol | 19 g |
| Xanthan gum | 0.0125 g |

The desired gel preparation was obtained by using the above respective ingredients in the same manner as in Production Example 5. The viscosity of the solution at 50° C. was adjusted to 105 cP.

Production Example 10 (Gel volume was set at ¼ of that in Production Example 7)

| Calcium polystyrene sulfonate (particle size distribution: 5–50 μm) | 5 g |
|---|---|
| Agar | 0.25 g |
| Purified water | 10 ml |
| Red wine | 5 ml |
| D-sorbitol | 9.5 g |
| Xanthan gum | 0.0063 g |

The desired gel preparation was obtained by using the above respective ingredients in the same manner as in Production Example 5. The viscosity of the solution at 50° C. was adjusted to 335 cP.

Production Example 11

| Calcium polystyrene sulfonate (particle size distribution: 5–50 μm) | 5 g |
|---|---|
| Agar | 1 g |
| Purified water | 30 ml |
| Coffee extract | suitable amount |
| D-sorbitol | 50 g |
| Propylene glycol | 20 g |
| Xanthan gum | 0.16 g |

The above respective ingredients were used to prepare the calcium polystyrene sulfonate-containing gel preparation. That is, agar as a gelling agent was heated and dissolved in purified water, then propylene glycol was added, and D-sorbitol containing xanthan gum as a thickening agent dispersed therein was added and mixed therewith. The resulting solution was filtered, the coffee extract was added to the filtrate and cooled to 50° C., calcium polystyrene sulfonate was added and mixed uniformly therewith, and the mixture was dispensed into a vessel and cooled in a refrigerator to obtain the desired gel preparation. The viscosity of the solution at 50° C. was adjusted to 4200 cP.

Production Example 12

| Calcium polystyrene sulfonate (particle size distribution: 5–50 μm) | 5 g |
|---|---|
| Agar | 1 g |
| Purified water | 20 ml |
| Coffee extract | suitable amount |
| Glycerin | 80 g |
| Xanthan gum | 0.16 g |

The desired gel preparation was obtained by using the above respective ingredients in the same manner as in Production Example 11. The viscosity of the solution at 50° C. was adjusted to 1675 cP.

Production Example 13

| | |
|---|---|
| Calcium polystyrene sulfonate | 5 g |
| (particle size distribution: 5–50 μm) | |
| Agar | 0.5 g |
| Purified water | 15 ml |
| Coffee extract | suitable amount |
| D-sorbitol | 35 g |
| Sodium sorbate | 0.05 g |
| Xanthan gum | 0.08 g |

The desired gel preparation was obtained by using the above respective ingredients in the same manner as in Production Example 11. The viscosity of the solution at 50° C. was adjusted to 1075 cP.

Production Example 14

| | |
|---|---|
| Calcium polystyrene sulfonate | 5 g |
| (particle size distribution: 5–50 μm) | |
| Agar | 0.35 g |
| Purified water | 20 ml |
| Red wine | 10 ml |
| Powdered malt starch hydrolysate | 20 g |
| Sodium sorbate | 0.05 g |
| Xanthan gum | 0.08 g |

The desired gel preparation was obtained by using the above respective ingredients in the same manner as in Production Example 5. The viscosity of the solution at 50° C. was adjusted to 500 cP.

Production Example 15

| | |
|---|---|
| Calcium polystyrene sulfonate | 5 g |
| (particle size distribution: 5–50 μm) | |
| Agar | 0.5 g |
| Purified water | 15 ml |
| Red wine | 10 ml |
| Sucrose | 25 g |
| Xanthan gum | 0.08 g |

The desired gel preparation was obtained by using the above respective ingredients in the same manner as in Production Example 5. The viscosity of the solution at 50° C. was adjusted to 1400 cP.

Production Example 16 (Successive production of the gel preparation corresponding to Production Example 7)

| | |
|---|---|
| Calcium polystyrene sulfonate | 250 g |
| (particle size distribution: 5–50 μm) | |
| Agar | 50 g |
| Purified water | 2100 ml |
| Red wine | 1000 ml |
| D-sorbitol | 1900 g |
| Carboxymethyl cellulose-Na (CMC-Na) | 2 g |

The above respective ingredients were used to successively prepare the calcium polystyrene sulfonate-containing gel preparation. That is, agar as a gelling agent was heated and dissolved in purified water, then red wine was added, and D-sorbitol containing sodium carboxymethyl cellulose as a thickening agent dispersed therein was added and mixed therewith. The resulting solution was filtered and cooled to 50° C., and calcium polystyrene sulfonate was added and mixed uniformly therewith by a propeller mixer. Further, the mixture was dispensed in a predetermined amount into vessels by means of a dispensing machine under stirring by the propeller mixer and then cooled in a refrigerator to obtain the desired gel preparation. The viscosity of the solution at 50° C. was adjusted to 110 cP.

Production Example 17 (Pudding preparation)

| | |
|---|---|
| Calcium polystyrene sulfonate | 5 g |
| (particle size distribution: 5–50 μm) | |
| Milk | 40 ml |
| Gelatin | 4 g |
| Purified water | 12 ml |
| D-sorbitol | 40 g |
| Orange flavor | 1 drop |
| Modified starch | 0.5 g |
| Xanthan gum | 0.05 g |
| Guar gum | 0.45 g |

The above respective ingredients were used to prepare the calcium polystyrene sulfonate-containing gel preparation. That is, gelatin as a gelling agent was swollen in purified water, and milk and D-sorbitol were added, heated and dissolved. Orange flavor, modified starch, xanthan gum and guar gum were added and mixed therewith, the resulting solution was filtered and cooled to 50° C., calcium polystyrene sulfonate was added and mixed uniformly therewith, and the mixture was dispensed into a vessel and cooled in a refrigerator to obtain the desired pudding preparation. The viscosity of the solution at 50° C. was adjusted to 155 cP.

Production Example 18 (Jelly preparation: Carrageenan jelly)

| | |
|---|---|
| Calcium polystyrene sulfonate | 5 g |
| (particle size distribution: 5–50 μm) | |
| Carrageenan | 0.2 g |
| Locust bean gum | 0.17 g |
| Sodium dihydrogen phosphate | 0.045 g |
| Calcium lactate | 0.015 g |
| D-sorbitol | 15 g |
| Citric acid | 0.04 g |
| Sodium citrate | 0.015 g |
| Purified water | 35 ml |
| Orange flavor | 0.6 g |
| Xanthan gum | 0.08 g |

The above respective ingredients were used to prepare the calcium polystyrene sulfonate-containing gel preparation. That is, carrageenan, locust bean gum, sodium dihydrogen phosphate and calcium lactate were dispersed in D-sorbitol, and purified water was added, and the mixture was dissolved by heating at 80° C. Orange flavor, citric acid, sodium citrate and xanthan gum were added to said solution and stirred, the resulting solution was cooled to 50° C., calcium polystyrene sulfonate was added and mixed uniformly therewith, and the mixture was dispensed into a vessel and cooled in a refrigerator to obtain the desired jelly preparation. The viscosity of the solution at 50° C. was adjusted to 1050 cP.

Production Example 19 (Jelly preparation: Mannan jelly)

| | |
|---|---|
| Calcium polystyrene sulfonate (particle size distribution: 5–50 μm) | 5 g |
| Glucomannan | 0.25 g |
| Carrageenan | 0.35 g |
| Citric acid | 0.16 g |
| D-sorbitol | 34.8 g |
| Purified water | 50 ml |
| Orange juice | 8 g |
| Orange flavor | 1 drop |
| Xanthan gum | 0.08 g |

The above respective ingredients were used to prepare the calcium polystyrene sulfonate-containing gel preparation. That is, glucomannan and carrageenan were swollen in purified water and dissolved by heating at 85° C. D-sorbitol, citric acid and xanthan gum were added to and dissolved in this solution, and after the resulting solution was cooled to 50° C., orange flavor, orange juice and calcium polystyrene sulfonate were added, mixed uniformly, and the mixture was dispensed into a vessel and cooled in a refrigerator to obtain the desired jelly preparation. The viscosity of the solution at 50° C. was adjusted to 120 cP.

Production Example 20 (Gummi.jelly preparation)

| | |
|---|---|
| Calcium polystyrene sulfonate (particle size distribution: 5–50 μm) | 5 g |
| D-sorbitol | 25 g |
| Hydrogenated malt starch hydrolysate | 37 g |
| Gelatin | 9 g |
| Citric acid | 0.4 g |
| Purified water | 24 ml |
| Paprika coloring matter | 0.07 g |
| Vegetable coloring matter | 0.02 g |
| White peach oil | 0.2 g |
| Peach juice concentrated to ⅕ | 2.0 g |

The above respective ingredients were used to prepare the calcium polystyrene sulfonate-containing gel preparation. That is, gelatin as a gelling agent was added to 23 ml purified water and dissolved at 60° C. Citric acid was added to 1 ml purified water and heated at 60° C. Then, D-sorbitol and the starch hydrolysate were heated to 115° C., and the previously prepared gelatin solution and citric acid solution described above, as well as the coloring, matters, flavor and juice were added and mixed therewith. The resulting solution was cooled to 50° C., and calcium polystyrene sulfonate was added and mixed uniformly therewith, dispensed into a vessel, and dried whereby the desired gummi.jelly preparation was obtained. The viscosity of the solution at 50° C. was adjusted to 510 cP.

Production Example 21 (Semi-solid preparation)

| | |
|---|---|
| Calcium polystyrene sulfonate (particle size distribution: 5–50 μm) | 5 g |
| D-sorbitol | 5 g |
| Honey | 5 g |
| Modified starch | 2.25 g |
| Dextrin | 0.75 g |
| Purified water | 45 ml |

The above respective ingredients were used to prepare the calcium polystyrene sulfonate-containing gel preparation. That is, D-sorbitol and honey were added to water and dissolved by heating. Then, the modified starch and dextrin were added and dissolved, and after the resulting solution was cooled to 50° C., calcium polystyrene sulfonate was added and mixed uniformly therewith, and the mixture was dispensed into a vessel and cooled in a refrigerator whereby the desired semi-solid preparation was obtained. The viscosity of the solution at 50° C. was adjusted to 900 cP.

Production Example 22

| | |
|---|---|
| Calcium polystyrene sulfonate (particle size distribution: 5–50 μm) | 5 g |
| Powdered hydrogenated malt starch hydrolysate | 2 g |
| Agar | 0.07 g |
| Carrageenan | 0.03 g |
| Gelatin | 0.1 g |
| Pectin | 0.02 g |
| Sodium citrate | 0.28 g |
| Purified water | 17.5 ml |

The above respective ingredients were used to prepare the calcium polystyrene sulfonate-containing gel preparation. That is, sodium citrate, agar and carrageenan were dissolved by heating in purified water, and while the liquid temperature was kept at 70° C. or more, gelatin and pectin were added and dissolved. Further, the powdered hydogenated malt starch hydrolysate was added and dissolved, and the solution was cooled to 50° C., and calcium polystyrene sulfonate was added and mixed uniformly therewith. The resulting solution was dispensed into a vessel and cooled in a refrigerator, whereby the desired gel preparation was obtained. The viscosity of the solution at 50° C. was adjusted to 1000 cP.

Production Example 23

| | |
|---|---|
| Calcium polystyrene sulfonate (particle size distribution: 5–50 μm) | 5 g |
| D-sorbitol | 5 g |
| Agar | 0.14 g |
| Carrageenan | 0.07 g |
| Gelatin | 0.33 g |
| Pectin | 0.16 g |
| Citrate buffer (pH 6.3) | 14.3 ml |

The above respective ingredients were used to prepare the calcium polystyrene sulfonate-containing gel preparation. That is, agar and carrageenan were dissolved by heating in citrate buffer, pH 6.3, and while the solution temperature was kept at 70° C. or more, gelatin and pectin were added and dissolved. Further, D-sorbitol was added and dissolved, then the solution was cooled to 50° C., and calcium polystyrene sulfonate was added and mixed uniformly therewith. The resulting solution was dispensed into a vessel and cooled in a refrigerator, whereby the desired gel preparation was obtained. The viscosity of the solution at 50° C. was adjusted to 25000 cP.

Production Example 24

| | |
|---|---|
| Calcium polystyrene sulfonate (particle size distribution: 5–50 μm) | 5 g |
| Powdered hydrogenated malt starch hydrolysate | 5 g |
| Agar | 0.14 g |
| Pectin | 0.11 g |
| Citrate buffer (pH 6.3) | 14.75 ml |

The desired gel preparation was obtained by using the above respective ingredients in the same manner as in Production Example 23. The viscosity of the solution at 50° C. was adjusted to 1625 cP.

Production Example 25

| | |
|---|---|
| Calcium polystyrene sulfonate (particle size distribution: 5–50 μm) | 5 g |
| Powdered hydrogenated malt starch hydrolysate | 5 g |
| Agar | 0.07 g |
| Gelatin | 0.492 g |
| Citrate buffer (pH 6.3) | 14.438 ml |

The desired gel preparation was obtained by using the above respective ingredients in the same manner as in Production Example 23. The viscosity of the solution at 50° C. was adjusted to 105 cP.

Production Example 26

| | |
|---|---|
| Calcium polystyrene sulfonate (particle size distribution: 5–50 μm) | 5 g |
| D-sorbitol | 8 g |
| Hydrogenated malt starch hydrolysate | 4 g |
| Pectin | 0.568 g |
| Powdered sucrose | 0.84 g |
| Purified water | 9 ml |
| 50% citric acid solution | 0.24 ml |
| Flavor | suitable amount |

The above respective ingredients were used to prepare the calcium polystyrene sulfonate-containing gel preparation. That is, powdered sucrose containing pectin dispersed therein was heated and dissolved in purified water, and while the solution temperature was kept at 90° C. or more, the starch hydrolysate and D-sorbitol were added and dissolved. Further, calcium polystyrene sulfonate was added and mixed uniformly therewith, and just before their addition, the flavor and 50% citric acid solution was added and mixed. The resulting solution was dispensed at 50° C. or more into a vessel and cooled in a refrigerator, whereby the desired gel preparation was obtained. The viscosity of the solution at 50° C. was adjusted to 4760 cP.

Production Example 27

| | |
|---|---|
| Calcium polystyrene sulfonate, | |
| particle size distribution: 5–50 μm: | 4.75 g |
| particle size distribution: 90–100 μm: | 0.25 g |
| Agar | 1 g |
| Purified water | 42 ml |
| Red wine | 20 ml |
| D-sorbitol | 38 g |
| Carboxymethyl cellulose-Na (CMC-Na) | 0.04 g |

The desired gel preparation was obtained by using the above respective ingredients in the same manner as in Production Example 5. The viscosity of the solution at 50° C. was adjusted to 110 cP.

Control Production Example 1

| | |
|---|---|
| Calcium polystyrene sulfonate (commercial powdery preparation with a particle size distribution of 5–200 μm) | 5 g |
| Agar | 0.5 g |
| Purified water | 43.6 ml |
| Aspartame | 0.025 g |

The above respective ingredients were used to prepare the calcium polystyrene sulfonate-containing gel preparation. That is, agar as a gelling agent was heated and dissolved in purified water, and aspartame as a sweetener was added, mixed and dissolved. After the resulting solution was filtered and cooled to 50° C., calcium polystyrene sulfonate was added and mixed uniformly therewith, and the mixture was dispensed into a vessel and cooled in a refrigerator to obtain the desired gel preparation. The viscosity of the solution at 50° C. was 30 cP.

Control Production Example 2

| | |
|---|---|
| Calcium polystyrene sulfonate (commercial powdery preparation with a particle size distribution of 5–200 μm) | 5 g |
| Agar | 0.5 g |
| Carboxymethyl cellulose-Na (CMC-Na) | 0.9 g |
| Purified water | 43.6 ml |
| Aspartame | 0.025 g |

The desired gel preparation was obtained by using the above respective ingredients in the same manner as in Control Production Example 1. The viscosity of the solution at 50° C. was adjusted to 3750 cP.

Control Production Example 3

| | |
|---|---|
| Calcium polystyrene sulfonate (particle size distribution: 5–150 μm) | 5 g |
| Agar | 0.5 g |
| Carboxymethyl cellulose-Na (CMC-Na) | 0.9 g |
| Purified water | 43.6 ml |
| Aspartame | 0.025 g |

The desired gel preparation was obtained by using the above respective ingredients in the same manner as in Control Production Example 1. The viscosity of the solution at 50° C. was adjusted to 3700 cP.

Control Production Example 4 {Formulation according to the literature "Yakuri To Chiryo", Vol. 21, No. 6, p. 2017 (1993)}

| Calcium polystyrene sulfonate (commercial powdery preparation with a particle size distribution of 5–200 μm) | 5 g |
|---|---|
| Agar | 1 g |
| Purified water | 80 ml |
| Red wine | 20 ml |
| Sucrose | 10 g |

According to the method described in the literature, the above respective ingredients were used to prepare the calcium polystyrene sulfonate-containing gel preparation. That is, agar as a gelling agent was heated and dissolved in purified water, and then sucrose and red wine were added. After the resulting solution was filtered and cooled to 50° C., calcium polystyrene sulfonate was added, mixed uniformly therewith and poured into a vessel and cooled in a refrigerator to obtain the desired gel preparation. The viscosity of the solution at 50° C. was 35 cP.

Control Production Example 5 (Gel volume was set at ½ of that in Control Production Example 4)

| Calcium polystyrene sulfonate (commercial powdery preparation with a particle size distribution of 5–200 μm) | 5 g |
|---|---|
| Agar | 0.5 g |
| Purified water | 40 ml |
| Red wine | 10 ml |
| Sucrose | 5 g |

The gel preparation was obtained by using the above respective ingredients in the same manner as in Control Production Example 4. The viscosity of the solution at 50° C. was 35 cP.

Control Production Example 6

| Calcium polystyrene sulfonate (particle size distribution: 5–100 μm) | 5 g |
|---|---|
| Agar | 1 g |
| Purified water | 80 ml |
| Red wine | 20 ml |

The gel preparation was obtained by using the above respective ingredients in the same manner as in Control Production Example 4. The viscosity of the solution at 50° C. was 10 cP.

Control Production Example 7

| Calcium polystyrene sulfonate (particle size distribution: 5–75 μm) | 5 g |
|---|---|
| Agar | 1 g |

-continued

| Purified water | 80 ml |
|---|---|
| Red wine | 20 ml |

The gel preparation was obtained by using the above respective ingredients in the same manner as in Control Production Example 4. The viscosity of the solution at 50° C. was 10 cP.

Control Production Example 8

| Calcium polystyrene sulfonate (particle size distribution: 5–50 μm) | 5 g |
|---|---|
| Agar | 1 g |
| Purified water | 80 ml |
| Red wine | 20 ml |

The gel preparation was obtained by using the above respective ingredients in the same manner as in Control Production Example 4. The viscosity of the solution at 50° C. was 10 cP.

Control Production Example 9

| Calcium polystyrene sulfonate (particle size distribution: 5–25 μm) | 5 g |
|---|---|
| Agar | 1 g |
| Purified water | 80 ml |
| Red wine | 20 ml |

The gel preparation was obtained by using the above respective ingredients in the same manner as in Control Production Example 4. The viscosity of the solution at 50° C. was 10 cP.

Production Example 10 (Successive production of the gel preparation according to Control Production Example 4)

| Calcium polystyrene sulfonate (particle size distribution: 5–200 μm) | 250 g |
|---|---|
| Agar | 50 g |
| Purified water | 4000 ml |
| Red wine | 1000 ml |
| Sucrose | 500 g |

The above respective ingredients were used to successively prepare the calcium polystyrene sulfonate-containing gel preparation. That is, agar as a gelling agent was heated and dissolved in purified water, and then sucrose and red wine were added. After the resulting solution was filtered and cooled to 50° C., calcium polystyrene sulfonate was added and mixed uniformly therewith by a propeller mixer. Further, the mixture was dispensed in a predetermined amount into vessels by means of a dispensing machine under stirring by the propeller mixer and cooled in a refrigerator to obtain the gel preparation.

Test Example 2 (Organoleptic Test: Effect of particle diameter and dispersibility on sense of ingestion)

The gel or jelly preparations obtained in Production Examples 1 and 2 as well as Control Production Examples 1, 2 and 3 were examined by a panel of 5 members for the influence of the particle diameter and dispersibility of polystyrene sulfonate on a sense of ingestion or a sense of eating. In unpleasant cases, water was freely taken, and the amount of water for ingestion was measured in unit of 10 ml. The particle diameter of polystyrene sulfonate and the viscosity of the solution at 50° C. in these Production Examples and Control Production Examples are summarized in Table 1 below. With respect to the degree of sense of ingestion in the tables, a strong sense of roughness is expressed as sense of foreign matter (++ or more) in all the organoleptic tests in this specification.

TABLE 1

| Test preparation | Diameter of polystyrene sulfonate ($\mu$m) | Viscosity of solution at 50° C. (cP) |
| --- | --- | --- |
| Control Prodn. Ex. 1 | 5 200 (commercial product, not controlled) | 30 (not adjusted) |
| Control Prodn. Ex. 2 | 5 200 (same as above) | 3750 (adjusted) |
| Control Prodn. Ex. 3 | 5 150 (controlled) | 3700 (same as above) |
| Prodn. Ex. 1 | 5 100 (controlled) | 3500 (same as above) |
| Prodn. Ex. 2 | 5 50 (same as above) | 3300 (same as above) |

The results are as shown in the table below. That is, it is understood that the preparations in which the polystyrene sulfonate was controlled to make its particle diameter to 100 $\mu$m or less and was uniformly dispersed by adjusting the viscosity reduce the sense of foreign matter and the sense of roughness resulting from said salt significantly, thus making it unnecessary to drink excessive water.

TABLE 2

| Test preparation | Panelists and their evaluation | | | | |
| --- | --- | --- | --- | --- | --- |
| | 1 | 2 | 3 | 4 | 5 |
| Control Prodn. Ex. 1 | +++ 120 | +++ 90 | ++ 60 | +++ 100 | +++ 110 |
| Control Prodn. Ex. 2 | +++ 100 | ++ 60 | ++ 60 | +++ 80 | ++ 90 |
| Control Prodn. Ex. 3 | ++ 80 | ++ 50 | + 40 | ++ 60 | + 70 |
| Prodn. Ex. 1 | + 30 | ± 0 | ± 20 | ± 20 | ± 0 |
| Prodn. Ex. 2 | ± 20 | – 0 | ± 20 | – 0 | – 0 |

Upper column: Sense of ingestion
−: No toughness is felt.
±: Slight roughness is felt.
+: Roughness is felt.
++: A sense of foreign matter is felt.
+++: A significant sense of foreign matter is felt.
Lower column: Amount of water for ingestion (ml)

Test Example 3 (Organoleptic Test:Comparison with the prior art)

The gel or jelly preparations obtained in Production Example 4 and Control Production Example 4 [literature Yakuri To Chiryo, Vol. 21, No. 6, p. 2017 (1993)] as well as a commercial powdery preparation suspended in 50 ml water in accordance with the conventional application method, were examined by a panel of 5 members for a sense of ingestion and a sense of eating. In unpleasant cases, water was freely taken in the same manner as in Test Example 2.

The results are shown in Table 3 below. That is, when the polystyrene sulfonate was suspended in 50 ml water and administered in accordance with the conventional application method for commercial powdery preparations, a significant sense of foreign matter of said salt is felt, so 96 ml water in average was further taken, and the total intake of water including water for suspension was 146 ml. In case of Control Production Example 4 which is the conventional polystyrene sulfonate-containing gel preparation, the sense of foreign matter of said salt was improved slightly as compared with an aqueous suspension, but 68 ml water in average was further taken. In case of Control Example 4, the amount of water in the preparation was as high as 100 ml, resulting in the intake of 168 ml of water in total. According to the conventional administration method and preparations, 438 ml and 504 ml water was taken in total respectively, when they were administered 3 times per day. On the other hand, the sense of foreign matter and the sense of roughness of the products of the present invention were considerably reduced, so it was not necessary to drink excessive water for administration, and the total intake of water including water contained in the preparation was 38 ml in average, resulting in the intake of 114 ml of water per day. This water intake is about ¼ of the water intake upon administration of the aqueous suspension, or about ⅓ of the water intake upon administration of Control Production Example 4.

TABLE 3

| Test preparation | Panelists and their evaluation | | | | |
| --- | --- | --- | --- | --- | --- |
| | 1 | 2 | 3 | 4 | 5 |
| Prodn. Ex. 4 | ± 20 54 | – 0 34 | – 0 34 | – 0 34 | ± 0 34 |
| Control Prodn. Ex. 4 | ++ 90 190 | ++ 60 160 | ++ 50 150 | ++ 60 160 | +++ 80 180 |
| Aqueous (50 ml) suspension of commercial powdery prepn. | +++ 110 160 | +++ 90 140 | +++ 80 130 | +++ 100 150 | +++ 100 150 |

Upper column: Sense of ingestion
−: No roughness is felt.
±: Slight roughness is felt.
+: Roughness is felt.
++: A sense of foreign matter is felt.
+++: A significant sense of foreign matter is felt.
Middle column: Amount of water for ingestion (ml)
Lower column: Total intake of water (ml)

Test Example 4 (Organoleptic Test: Effect of water-displacing agent)

The gel or jelly preparations obtained in Production Examples. 1, 2, 3 and 4 were examined by a panel of 5 members for the influence of a water-displacing agent on a sense of ingestion and a sense of eating. In unpleasant cases, water was freely taken in the same manner as in Test Example 2. The preparations in Production Examples 3 and 4 were prepared by adding powdered hydrogenated malt starch hydrolysate as the water-displacing agent to the preparations in Production Examples 1 and 2, respectively.

The results are shown in Table 4 below. It is understood that regardless of whether the water-substitute agent is present or not, the products of the present invention significantly reduce the sense of foreign matter and the sense of roughness resulting from the polystyrene sulfonate. If the water-displacing agent is added, it is recognized that the sense of foreign matter and the sense of roughness are further improved and the amount of excessively taken water tends to further decrease.

TABLE 4

| Test preparation | Panelists and their evaluation | | | | |
|---|---|---|---|---|---|
| | 1 | 2 | 3 | 4 | 5 |
| Prodn. Ex. 1 | +<br>30 | ±<br>0 | ±<br>20 | ±<br>20 | ±<br>0 |
| Prodn. Ex. 2 | ±<br>20 | −<br>0 | ±<br>20 | ±<br>0 | −<br>0 |
| Prodn. Ex. 3 (water-displacing agent added) | ±<br>20 | ±<br>0 | −<br>0 | ±<br>20 | −<br>0 |
| Prodn. Ex. 4 (water-displacing agent added) | ±<br>20 | −<br>0 | −<br>0 | −<br>0 | ±<br>0 |

Upper column: Sense of ingestion
−: No roughness is felt.
±: Slight roughness is felt.
+: Roughness is felt.
++: A sense of foreign matter is felt.
+++: A significant sense of foreign matter is felt.
Lower column: Amount of water for ingestion (ml)

Test Example 5 (Organoleptic Test: Effect of the products of the invention)

The gel or jelly preparations obtained in Production Examples 5, 6, 7, 8 and 27 as well as Control Production Example 4 were examined by a panel of 5 members for a sense of ingestion and a sense of eating. The particle diameter of polystyrene sulfonate and the viscosity of a solution at 50° C. in these Production Examples and Control Production Example are summarized in Table 5 below.

TABLE 5

| Test preparation | Diameter of polystyrene sulfonate ($\mu$m) | Viscosity of solution at 50° C. (cP) |
|---|---|---|
| Prodn. Ex. 5 | 5  100 (controlled) | 1000 or more (1013) |
| Prodn. Ex. 6 | 5   75 (same as above) | 300 or more (302) |
| Prodn. Ex. 7 | 5–50 (same as above) | 100 or more (111) |
| Prodn. Ex. 8 | 5   25 (same as above) | 50 or more (54) |
| Prodn. Ex. 27 | 5   50 (same as above): 95%<br>90  100 (same as above): 5% | 100 or more (110) |
| Control Prodn. Ex. 4 | 5  200 (commercial product, not controlled) | 35 (but not adjusted) |

The results are shown in Table 6 below. It is recognized that as compared with the conventional gel preparation, the gel preparations of the present invention significantly reduce the sense of foreign matter and the sense of roughness upon ingestion and intake.

TABLE 6

| Test preparation | Panelists and their evaluation | | | | |
|---|---|---|---|---|---|
| | 1 | 2 | 3 | 4 | 5 |
| Prodn. Ex. 5 | + | ± | ± | ± | + |
| Prodn. Ex. 6 | ± | ± | ± | − | ± |
| Prodn. Ex. 7 | − | − | ± | − | ± |
| Prodn. Ex. 8 | − | − | ± | − | − |

TABLE 6-continued

| Test preparation | Panelists and their evaluation | | | | |
|---|---|---|---|---|---|
| | 1 | 2 | 3 | 4 | 5 |
| Prodn. Ex. 27 | − | ± | ± | − | ± |
| Control Prodn. Ex. 4 | ++ | ++ | ++ | ++ | ++ |

−: No roughness is felt.
±: Slight roughness is felt.
+: Roughness is felt.
++: A sense of foreign matter is felt.
+++: A significant sense of foreign matter is felt.

Test Example 6 (Organoleptic Test: Effect of gel volume on sense of ingestion)

The gel or jelly preparations obtained in Production Examples 7, 9 and 10 as well as Control Production Examples 4 and 5 were examined by a panel of 5 members for the influence of gel volume on a sense of ingestion. The particle diameter of polystyrene sulfonate and the viscosity of a solution at 50° C. in these Production Examples and Control Production Examples are summarized in Table 7 below.

TABLE 7

| Test preparation | Diameter of polystyrene Sulfonate ($\mu$m) | Viscosity of soln. at 50° C. (cP) | Gel volume (relative value) |
|---|---|---|---|
| Prodn. Ex. 7 | 5  50 (controlled) | 100 or more (111) | 1 |
| Prodn. Ex. 9 | 5  50 (same as above) | 100 or more (105) | ½ |
| Prodn. Ex. 10 | 5  50 (same as above) | 100 or more (335) | ¼ |
| Control Prodn. Ex. 4 | 5  200 (commercial product, not controlled) | 35 (not adjusted) | 1 |
| Control Prodn. Ex. 5 | | 35 (not adjusted) | ½ |

The results are shown in Table 8 below. In case of conventional gel preparations according to the Control Production Examples, the sense of foreign matter upon intake is significantly increased when the gel volume is set to be low, whereas in case of the gel preparations of the present invention, the sense of ingestion was worsened very little even if the gel volume was set to be low.

TABLE 8

| Test preparation | Panelists and their evaluation | | | | |
|---|---|---|---|---|---|
| | 1 | 2 | 3 | 4 | 5 |
| Prodn. Ex. 7 | − | − | ± | − | ± |
| Prodn. Ex. 9 | ± | − | ± | ± | ± |
| Prodn. Ex. 10 | ± | ± | ± | ± | + |
| Control Prodn. Ex. 4 | ++ | ++ | ++ | ++ | ++ |
| Control Prodn. Ex. 5 | +++ | +++ | +++ | +++ | +++ |

−: No roughness is felt.
±: Slight roughness is felt.
+: Roughness is felt.
++: A sense of foreign matter is felt.
+++: A significant sense of foreign matter is felt.

Test Example 7 (Dispersibility of Polystyrene Sulfonate in Gel Preparation)

The preparations obtained in Production Examples 1 and 2 Control Production Examples 1, 2 and 3 used in Test Example 2 were examined for dispersibility of polystyrene sulfonate in the gel preparations. That is, each of the sample gel preparations (cylindrical form) was cut into 5 equal round slices at about 1 cm intervals to prepare test samples I to V in this order from the top. After these samples were separately heated and melted, and the resulting sol was filtered through a glass filter (G4), the residue (polystyrene sulfonate) on the filter was washed with about 100 ml of hot water and dried at 80° C. for 5 hours under reduced pressure, and the weight of the polystyrene sulfonate was measured. The particle diameter of polystyrene sulfonate and the viscosity of a solution at 50° C. in these Production Examples and Control Production Examples are summarized in Table 9 below.

TABLE 9

| Test preparation | Diameter of polystyrene sulfonate (μm) | Viscosity of solution at 50° C. (cP) |
|---|---|---|
| Prodn. Ex. 1 | 5–100 (controlled) | 3500 (adjusted) |
| Prodn. Ex. 2 | 5–50 (same as above) | 3300 (same as above) |
| Control Prodn. Ex. 1 | 5–200 (commercial product, not controlled) | 30 (not adjusted) |
| Control Prodn. Ex. 2 | 5–200 (same as above) | 3750 (adjusted) |
| Control Prodn. Ex. 3 | 5–150 (controlled) | 3700 (same as above) |

The results are shown in Table 10 below. That is, in Production Examples 1 and 2 as well as Control Production Examples 2 and 3, excluding Control Production Example 1, the content of polystyrene sulfonate in the uppermost sample I was almost the same as in the lowermost sample V. This means that said salt is uniformly dispersed in the gel preparations.

TABLE 10

| | Content (%) of polystyrene sulfonate in each part of gel preparation | | | | |
|---|---|---|---|---|---|
| Test preparation | I | II | III | IV | V |
| Prodn. Ex. 1 | 19.5 | — | — | — | 20.2 |
| Prodn. Ex. 2 | 19.8 | — | — | — | 20.1 |
| Control Prodn. Ex. 1 | 5.8 | | | | 58.2 |
| Control Prodn. Ex. 2 | 19.2 | — | — | — | 20.9 |
| Control Prodn. Ex. 3 | 19.4 | — | — | — | 20.3 |

Test Example 8 (Dispersibility of Polystyrene Sulfonate in Gel Preparation)

The preparations in Production Examples 5, 6, 7, 8 and 27 as well as Control Production Examples 4, 6, 7, 8 and 9 were examined for dispersibility of polystyrene sulfonate in the gel preparations by the method described in Test Example 7. The particle diameter of polystyrene sulfonate and the viscosity of a solution at 50° C. in these Production Examples and Control Production Examples are summarized in Table 11 below.

TABLE 11

| Test preparation | Diameter of polystyrene sulfonate (μm) | Viscosity of a solution at 50° C. (cP) |
|---|---|---|
| Prodn. Ex. 5 | 5–100 (controlled) | Adjusted to 1013 |
| Prodn. Ex. 6 | 5–75 (same as above) | Adjusted to 302 |
| Prodn. Ex. 7 | 5–50 (same as above) | Adjusted to 111 |
| Prodn. Ex. 8 | 5–25 (same as above) | Adjusted to 54 |
| Prodn. Ex. 27 | 5–50 (same as above): 95% 90–100 (same as above): 5% | Adjusted to 110 |
| Control Prodn. Ex. 4 | 5–200 (not controlled) | 35 (not adjusted) |
| Control Prodn. Ex. 6 | 5–100 (controlled) | 10 (not adjusted) |
| Control Prodn. Ex. 7 | 5–75 (same as above) | 10 (not adjusted) |
| Control Prodn. Ex. 8 | 5–50 (same as above) | 10 (not adjusted) |
| Control Prodn. Ex. 9 | 5–25 (same as above) | 10 (not adjusted) |

The results are shown in Table 12 below. In the gel preparations (cylindrical form) of the present invention, the content of polystyrene sulfonate in the uppermost sample I was almost the same as in the lowermost sample V, so it is understood that said salt is uniformly dispersed in the gel preparations. On the other hand, in the gel preparations of the Control Production Examples, a significant difference in the content of polystyrene sulfonate was observed between samples I and V, so it is recognized that precipitation of the salt particles occurs during solidification, after the solution was dispensed into a vessel.

TABLE 12

| | Content (%) of polystyrene sulfonate in each part of gel preparation | | | | |
|---|---|---|---|---|---|
| Test preparation | I | II | III | IV | V |
| Prodn. Ex. 5 | 20.6 | — | — | — | 20.3 |
| Prodn. Ex. 6 | 18.0 | — | — | — | 18.3 |
| Prodn. Ex. 7 | 19.2 | — | — | — | 20.6 |
| Prodn. Ex. 8 | 19.7 | — | — | — | 20.1 |
| Prodn. Ex. 27 | 19.0 | — | — | — | 20.8 |
| Control Prodn. Ex. 4 | 6.2 | 7.2 | 9.9 | 20.2 | 56.5 |
| Control Prodn. Ex. 6 | 7.5 | — | — | — | 37.9 |
| Control Prodn. Ex. 7 | 8.8 | — | — | — | 27.4 |
| Control Prodn. Ex. 8 | 6.1 | — | — | — | 28.1 |
| Control Prodn. Ex. 9 | 10.2 | — | — | — | 22.2 |

Test Example 9 (Uniformity of Polystyrene Sulfonate Content Among Gel Preparations)

The gel preparations of Production Example 16 and Control Production Example 10 were examined for the polyethylene sulfonate content among the individual preparations. That is, 10 gel preparations obtained by successive production using a dispersing machine were selected at random and separately heated and melted. After the resulting sol was filtered through a glass filter (G4), the residue (polystyrene sulfonate) on the filter was washed with about 100 ml of hot water, dried at 80° C. for 5 hours under reduced pressure and the weight of the polystyrene sulfonate was measured. The particle diameter of polystyrene sulfonate and the viscosity of a solution at 50° C. in these Production Example and Control Production Example are summarized in Table 13 below.

TABLE 13

| Test preparation | Diameter of polystyrene Sulfonate (μm) | Viscosity of solution at 50° C. (cP) |
|---|---|---|
| Prodn. Ex. 16 | 5–100 (controlled) | Adjusted to 110 |
| Control Prodn. Ex. 10 | 5–200 (not controlled) | 35 (not adjusted) |

The results are shown in Table 14 below. The average content of polystyrene sulfonate in the preparations of Production Example 16 was an approximately prescribed content, but the average content in the preparations of Control Production Example 10 was lower by about 20% than the prescribed amount, thus failing to conform to standards as a pharmaceutical preparation. The content of polystyrene sulfonate in individual preparations in Production Example 16 hardly deviated from the prescribed amount and was acceptable as a pharmaceutical preparation with less variability among individual preparations, while considerable variability was observed among gel preparations of Control Production Example 10, and the maximum deviation exceeded 15% (i.e. tolerance limit of variability among pharmaceutical preparations).

TABLE 14

| Test preparation | Average content (%, n = 10) | Maximum deviation (%) |
|---|---|---|
| Prodn. Ex. 16 | 98.8 | 4.0 |
| Control Prodn. Ex. 10 | 79.8 | 20.4 |

Test Example 10 (Measurement of Strength and Water Content of Gel Preparation)

The gel preparations obtained in Production Example 11, 12, 13, 14 and 15 as well as Control Production Example 4 were examined for strength. That is, each of the gel preparations was compressed at a predetermined rate with a rheometer (manufactured by Sun Kagaku Co., Ltd.), and the loading by which the gel was broken to greatly lower its stress was assumed to be the strength of the gel. Further, the gel was dried at 80° C. for 24 hours, and the reduction in the weight was calculated as the amount of water. The materials used as the water-substitute agent in the respective gel preparations are summarized in Table 15.

TABLE 15

| Test preparation | Materials used as water-substitute Agent |
|---|---|
| Prodn. Ex. 11 | D-sorbitol and propylene glycol |
| Prodn. Ex. 12 | Glycerin |
| Prodn. Ex. 13 | D-sorbitol |
| Prodn. Ex. 14 | Powdered hydrogenated malt[ose] starch hydrolysate [syrup] |
| Prodn. Ex. 15 | Sucrose |
| Control Prodn. Ex. 4 | None (Water content was not adjusted) |

The results are shown in Table 16. The amount of water in the gel preparations of the present invention, as compared with the conventional gel preparation as the control, was reduced by about 40% or more by replacing water by sugar alcohol etc. Any of the gel preparations according to the present invention maintained shape-retaining strength and were superior in the sense of ingestion upon intake, in comparison with the gel preparation in the Control Production Example.

TABLE 16

| Test preparation | Gel strength (g/cm$^2$) | Amount of water (%) |
|---|---|---|
| Prodn. Ex. 11 | 571 | 28.9 |
| Prodn. Ex. 12 | 451 | 18.5 |
| Prodn. Ex. 13 | 562 | 25.7 |
| Prodn. Ex. 14 | 379 | 53.0 |
| Prodn. Ex. 15 | 725 | 44.1 |
| Control Prodn. Ex. 4 | 272 | 85.1 |

INDUSTRIAL APPLICABILITY

The polystyrene sulfonate-containing preparation according to the present invention is a drug for therapy of hyperpotassemia. The gel preparation according to the present invention does not cause a sense of foreign matter or a sense of roughness in the oral cavity upon ingestion and intake, thus making it unnecessary to drink water for the ingestion, and further its water content is low, so that control of water intake is made easy in the case of a patient with renal insufficiency who is subject to restrict intake of water, resulting in significant improvement in the quality of life of the patient. Further, it can be expected that compliance with clinician s instructions is improved, and as a result, its stable pharmaceutical effect is expected. Further, because there is no or less variability in the amount of the active ingredient among individual pharmaceutical preparations, the preparation conforms to standards as a pharmaceutical preparation and its large-scale production at the industrial level is feasible.

What is claimed is:

1. A method for treating hyperpotassemia caused by renal insufficiency, wherein a pharmaceutical gel preparation is administered to a patient in need of treatment, which comprises a gelling agent, a thickening agent, water, and polystyrene sulfonate and is characterized in that the particle size is within the range of 5–100 μm, the viscosity of the preparation with dispersed polystyrene sulfonate particles before gelation is adjusted depending on the particle size by adding the thickening agent, and the polystyrene sulfonate particles after gelation are uniformly dispersed.

2. The method according to claim 1, wherein the pharmaceutical gel preparation further comprises at least one water displacing agent selected from the group consisting of glycerin, propylene glycol, polyethylene glycols, sugars and sugar alcohols, wherein a part of the water of the preparation is substituted by the water displacing agent.

3. The method according to claim 1, wherein the viscosity of the pharmaceutical gel preparation at 50° C. before gelation is 50 cP or more where the particle diameter of polystyrene sulfonate is 5 to 25 μm, 100 cP or more where the particle diameter is 5–50 μm, 300 cP or more where the particle diameter is 5–75 μm, and 1000 cP or more where the particle diameter is 5–100 μm.

4. The method according to claim 1, wherein the water in the pharmaceutical gel preparation is 60 ml or less per 5 g of polystyrene solfonate.

5. The method according to claim 1, wherein the water in the pharmaceutical gel preparation is 12 ml to 20 ml per 5 g of polystyrene sulfonate.

* * * * *